(12) United States Patent  
Kim (10) Patent No.: US 12,370,543 B2  
(45) Date of Patent: Jul. 29, 2025

(54) REACTION WELL CARTRIDGE DEVICE AND REACTION WELL CARTRIDGE SYSTEM

(71) Applicant: MICRO DIGITAL CO., LTD., Gyeonggi-do (KR)

(72) Inventor: Kyung Nam Kim, Gyeonggi-do (KR)

(73) Assignee: MICRO DIGITAL CO., LTD., Gyeonggi-Do (KR)

( * ) Notice: Subject to any disclaimer, the term of this patent is extended or adjusted under 35 U.S.C. 154(b) by 847 days.

(21) Appl. No.: 17/601,954

(22) PCT Filed: Mar. 19, 2020

(86) PCT No.: PCT/KR2020/003762  
§ 371 (c)(1),  
(2) Date: Oct. 7, 2021

(87) PCT Pub. No.: WO2020/213840  
PCT Pub. Date: Oct. 22, 2020

(65) Prior Publication Data  
US 2022/0184603 A1    Jun. 16, 2022

(30) Foreign Application Priority Data  
Apr. 15, 2019 (KR) .................. 10-2019-0043900

(51) Int. Cl.  
*B01L 3/00* (2006.01)  
*G01N 33/543* (2006.01)

(52) U.S. Cl.  
CPC ........ *B01L 3/502* (2013.01); *G01N 33/54366* (2013.01); *B01L 2200/16* (2013.01);  
(Continued)

(58) Field of Classification Search  
CPC .......................... B01L 3/502; B01L 2300/069  
See application file for complete search history.

(56) References Cited

U.S. PATENT DOCUMENTS 6,271,040 B1    8/2001  Buechler  
7,429,356 B2    9/2008  Seto  
(Continued)

FOREIGN PATENT DOCUMENTS

JP    3635645 B1    4/2005  
JP    4911264 B2    4/2012  
(Continued)

*Primary Examiner* — Natalia Levkovich  
(74) *Attorney, Agent, or Firm* — Bridgeway IP Law Group, PLLC; Sang Ho Lee; Hyun Woo Shin (57) ABSTRACT

Provided are a reaction well cartridge device and reaction well cartridge system suitable for biochemical or biological reaction, the reaction well cartridge device including a cartridge body including at least one of a reaction well container containing a reaction well where biological reactions occur, pipette tip containers containing at least pipette tips, a sample container containing a sample, reagent containers containing reagents, a mixed solution container containing a mixed solution of the sample and the reagents, a diluent container containing a diluent, washing solution containers containing washing solutions, and combinations thereof, and a temporary storage provided on the cartridge body to temporarily store wastes produced after the reactions occur in the reaction well.

20 Claims, 7 Drawing Sheets

(52) U.S. Cl.
CPC ... *B01L 2300/041* (2013.01); *B01L 2300/047* (2013.01); *B01L 2300/069* (2013.01); *B01L 2400/0605* (2013.01)

(56) References Cited

U.S. PATENT DOCUMENTS

| | | |
|---|---|---|
| 8,404,489 B2 | 3/2013 | Akashi |
| 8,961,902 B2 | 2/2015 | Falb |
| 9,857,384 B2 | 1/2018 | Orning |
| 2009/0155123 A1* | 6/2009 | Williams ............... B01L 3/021 422/65 |

FOREIGN PATENT DOCUMENTS

| | | |
|---|---|---|
| KR | 20100135307 A | 12/2010 |
| KR | 20110072512 A | 6/2011 |
| KR | 20140090195 A | 7/2014 |

\* cited by examiner

REACTION WELL CARTRIDGE DEVICE AND REACTION WELL CARTRIDGE SYSTEM

TECHNICAL FIELD

The present invention relates to a reaction well cartridge device and reaction well cartridge system, and more particularly, to a reaction well cartridge device and reaction well cartridge system suitable for biochemical or biological reaction.

BACKGROUND ART

A variety of chemiluminescence (CL) methods have been developed in recent years, and examples thereof include enzyme immunoassay (EIA) using antigen-antibody reaction, chemiluminescence immunoassay (CLIA) where a chemiluminescent compound is used for labeling as a tracer for immunoassay, and chemiluminescent enzyme immunoassay (CLEIA) for detecting enzyme activity with high sensitivity by using a chemiluminescent compound in a detection system.

In these immunoassays, the presence and concentration of an analyte are detected based on biospecific binding between, for example, antigens and antibodies. Substances which do not participate in biospecific binding are washed away before a signal is measured.

The washing process may increase signal sensitivity by reducing a background signal.

Capillary-driven flow using capillary action is based on a phenomenon in which a fluid automatically flows due to surface tension without using an external pump. Many simple disposable immunoassay products using capillary-driven flow, e.g., pregnancy test kits, have been developed. Most of the products induce capillary-driven flow by using a porous material and may not be washed more than twice.

U.S. Pat. Registration No. 6,271,040 discloses induction of capillary-driven flow in microchannels without using a porous material. However, in the above-mentioned products and patent, although capillary action is used, only a single sample solution is used to wash a microfluid and thus a background signal due to the sample may not be easily removed.

As described above, effective washing technology has not been developed and much improvement thereof is required. Therefore, the development of a technology capable of simplifying a washing process based on fluid control in a reaction well, of facilitating manufacturing of cartridges, and of rapidly and easily repeating the washing process is seriously required.

Meanwhile, a mixture of a sample, a reagent, a washing solution, etc. after an assay is discharged through a separate waste transfer line, and wastes discharged from a plurality of reaction wells are collected and stored in a waste storage tank and then are disposed of when the waste storage tank is full.

However, the wastes contained in large amounts in the waste storage tank may cause revulsion in appearance, and the wastes discharged from the plurality of reaction wells are already contaminated or easily contaminable by a variety of viruses and bacteria and may cause rapid bacterial growth or decay over time to broadly pollute the air or the environment as well as waste collection tubes or the waste storage tank.

DETAILED DESCRIPTION OF THE INVENTION

Technical Problem

The present invention provides a reaction well cartridge device and reaction well cartridge system capable of simplifying fluid control for biochemical reaction in a reaction well, of facilitating manufacturing of devices, of controlling the flow, stop, and washing of a fluid by using an active pump, of freely adjusting the number of washing processes, of achieving aesthetic appearance by temporarily storing wastes in a cartridge to be disposed of after a single use, and of achieving hygienic properties by preventing bacterial growth, decay, or leakage of the wastes, thereby increasing the safety of bioassays and preventing environmental pollution. However, the scope of the present invention is not limited thereto.

Technical Solution

According to an aspect of the present invention, there is provided a reaction well cartridge device including a cartridge body including at least one of a reaction well container containing a reaction well where biological reactions occur, pipette tip containers containing at least pipette tips, a sample container containing a sample, reagent containers containing reagents, a mixed solution container containing a mixed solution of the sample and the reagents, a diluent container containing a diluent, washing solution containers containing washing solutions, and combinations thereof, and a temporary storage provided on the cartridge body to temporarily store wastes produced after the reactions occur in the reaction well.

The temporary storage may include a waste storage case having an internal space, and a waste absorber contained in the internal space to absorb the wastes to prevent leakage of the wastes.

The waste absorber may be a dry compressed sponge capable of expanding and absorbing the wastes.

The waste absorber may include a coagulant that changes to a gel state when mixed with moisture, in order to prevent leakage of the wastes or environmental pollution caused by the wastes.

The waste absorber may include at least one of a disinfectant, a sanitizer, a deodorant, a preservative, bleach, an air freshener, a coagulant, and combinations thereof.

The waste storage case may include a middle case detachably coupled to a bottom surface of the cartridge body, and a lower case having a top opening to contain the waste absorber and detachably coupled to the middle case.

A waste passage through which the wastes pass may be provided through a side surface of the waste storage case, and a check valve may be mounted in the waste passage to prevent backflow of the wastes.

The temporary storage may be provided under a part including at least one of the sample container, the reagent containers, the mixed solution container, the diluent container, the washing solution containers, and combinations thereof.

The temporary storage may be provided under the reaction well container so as to be indirectly or directly connected to the reaction well.

According to another aspect of the present invention, there is provided a reaction well cartridge system including a reaction well cartridge device including a cartridge body including at least one of a reaction well container containing a reaction well where biological reactions occur, pipette tip containers containing at least pipette tips, a sample container containing a sample, reagent containers containing reagents, a mixed solution container containing a mixed solution of the sample and the reagents, a diluent container containing a diluent, washing solution containers containing washing solutions, and combinations thereof, and a temporary storage provided on the cartridge body to temporarily store wastes produced after the reactions occur in the reaction well, and a waste transfer device for transferring the wastes from the reaction well to the temporary storage.

The waste transfer device may include a first transfer line connected from the reaction well to the temporary storage, a first valve mounted on the first transfer line, and a first pump mounted on the first transfer line.

The temporary storage may be provided under a part including at least one of the sample container, the reagent containers, the mixed solution container, the diluent container, the washing solution containers, and combinations thereof, and the waste transfer device may include a second-1 transfer line curvedly connected from the reaction well to the temporary storage, a second-2 transfer line connected from the temporary storage to an external air vent, a second valve mounted on the second-2 transfer line, and a second pump mounted on the second-2 transfer line.

The temporary storage may be provided under the reaction well container so as to be indirectly or directly connected to the reaction well, and the waste transfer device may include a third-1 transfer line linearly connected from the reaction well to the temporary storage, a third-2 transfer line connected from the temporary storage to an external air vent, a third valve mounted on the third-2 transfer line, and a third pump mounted on the third-2 transfer line.

Advantageous Effects

As described above, according to some embodiments of the present invention, fluid control for biochemical reaction in a reaction well may be simplified, manufacturing of devices may be facilitated, the flow, stop, and washing of a fluid may be controlled using an active pump, the number of washing processes may be freely adjusted, aesthetic appearance may be achieved by temporarily storing wastes in a cartridge to be disposed of after a single use, and hygienic properties may be achieved by preventing bacterial growth, decay, or leakage of the wastes, thereby increasing the safety of bioassays and preventing environmental pollution. However, the scope of the present invention is not limited to the above-described effects.

BEST MODE

Hereinafter, the present invention will be described in detail by explaining embodiments of the invention with reference to the attached drawings.

The invention may, however, be embodied in many different forms and should not be construed as being limited to the embodiments set forth herein; rather, these embodiments are provided so that this disclosure will be thorough and complete, and will fully convey the concept of the invention to one of ordinary skill in the art. In the drawings, the thicknesses or sizes of layers are exaggerated for clarity and convenience of explanation.

Figure 1:
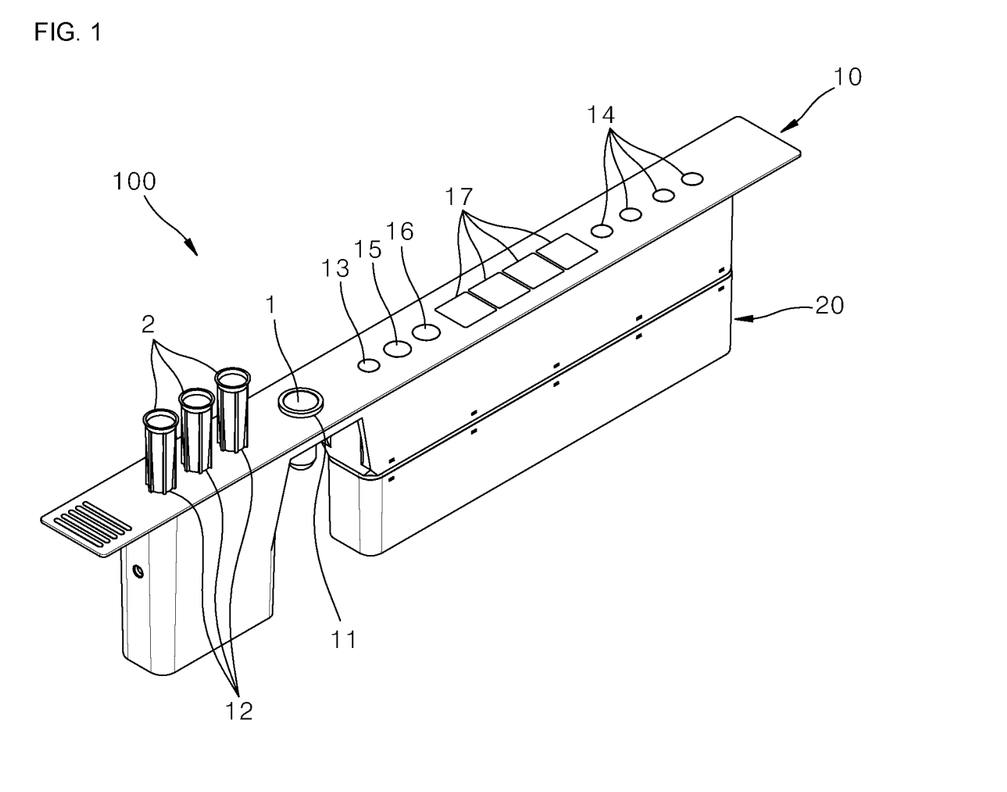
FIG. 1 is an exterior perspective view of a reaction well cartridge device according to some embodiments of the present invention.
Figure 2:
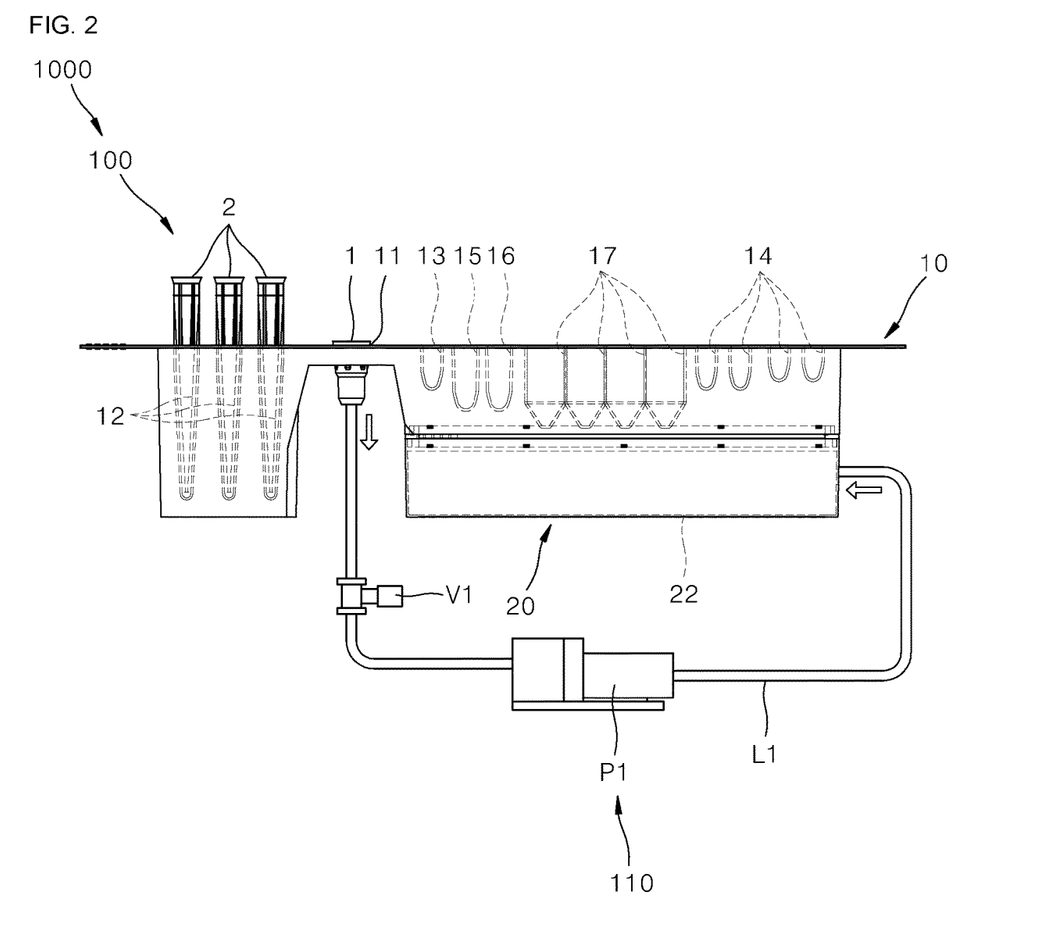
FIG. 2 is a front view of the reaction well cartridge device of FIG. 1 and a reaction well cartridge system.
Figure 3:
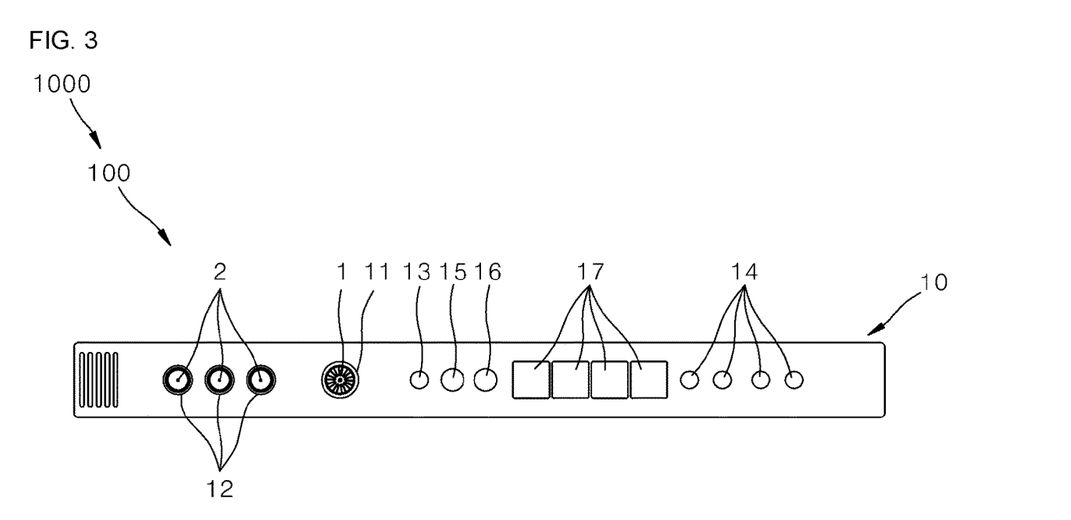
FIG. 3 is a plan view of the reaction well cartridge device of FIG. 1 and the reaction well cartridge system.
Figure 4:
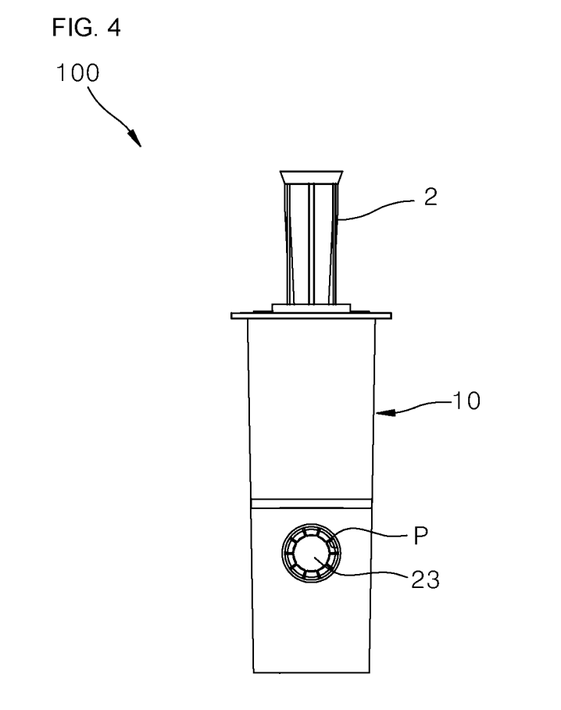
FIG. 4 is a side view of the reaction well cartridge device of FIG. 1.
Figure 5:
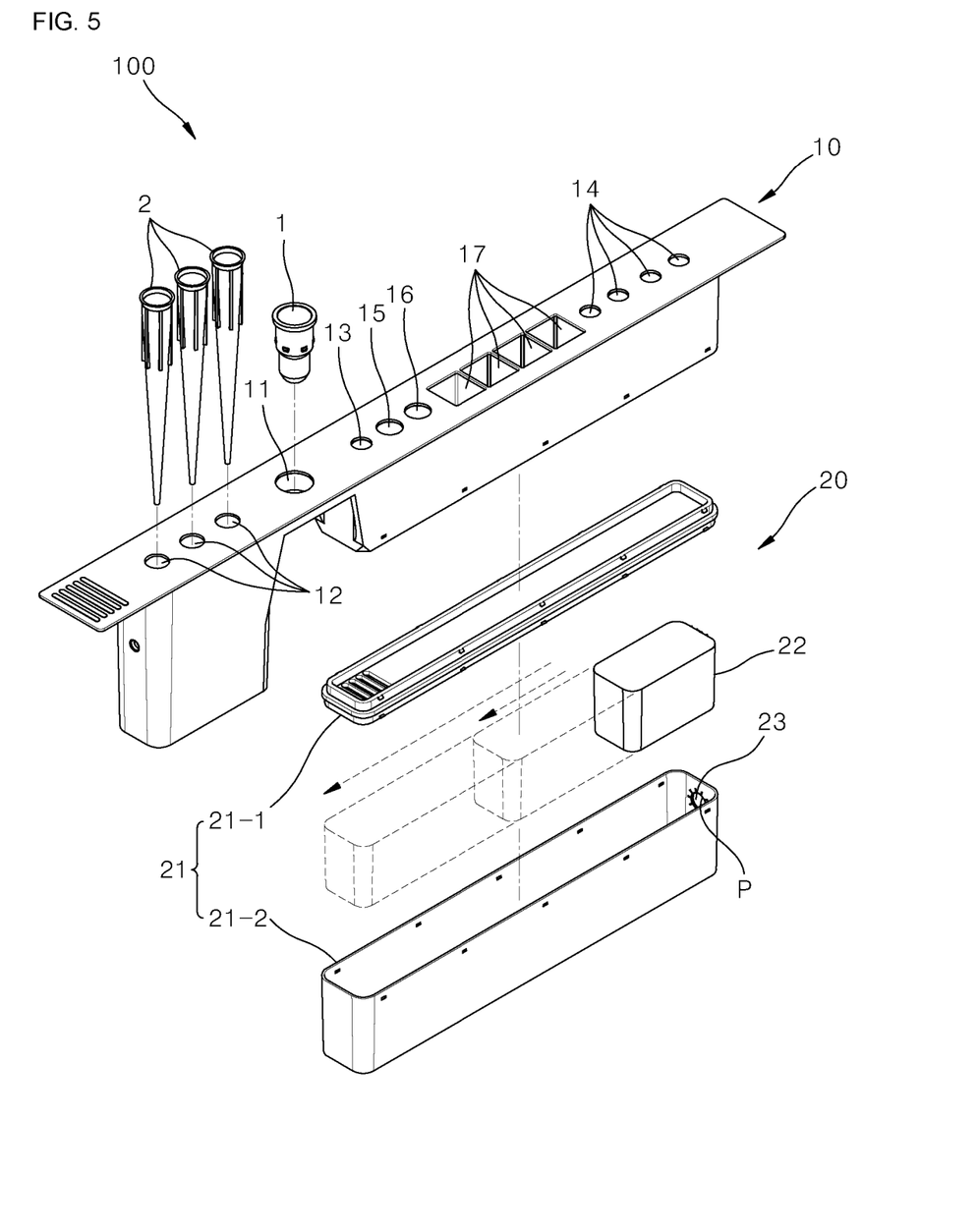
FIG. 5 is an exploded perspective view of the reaction well cartridge device of FIG. 1.

FIG. 1 is an exterior perspective view of a reaction well cartridge device 100 according to some embodiments of the present invention, FIG. 2 is a front view of the reaction well cartridge device 100 of FIG. 1 and a reaction well cartridge system 1000, FIG. 3 is a plan view of the reaction well cartridge device 100 of FIG. 1 and the reaction well cartridge system 1000, FIG. 4 is a side view of the reaction well cartridge device 100 of FIG. 1, and FIG. 5 is an exploded perspective view of the reaction well cartridge device 100 of FIG. 1.

Initially, as illustrated in FIGS. 1 to 5, the reaction well cartridge device 100 according to some embodiments of the present invention may mainly include a cartridge body 10 and a temporary storage 20.

For example, as illustrated in FIGS. 1 to 5, the cartridge body 10 may be a multi-container part formed of resin and including at least one of a reaction well container 11 containing a reaction well 1 where biological reactions occur, pipette tip containers 12 containing at least pipette tips 2, a sample container 13 containing a sample, reagent containers 14 containing reagents, a mixed solution container 15 containing a mixed solution of the sample and the reagents, a diluent container 16 containing a diluent, washing solution containers 17 containing washing solutions, and combinations thereof.

For example, as illustrated in FIGS. 1 to 5, the temporary storage 20 may be another container part attached to or integrated with the cartridge body 10 to temporarily store wastes produced after the reactions occur in the reaction well 1.

Specifically, for example, as illustrated in FIGS. 1 to 5, the temporary storage 20 may include a waste storage case 21 having an internal space, and a waste absorber 22 contained in the internal space to absorb the wastes to prevent leakage of the wastes.

Herein, for example, the waste absorber 22 may be a dry compressed sponge capable of expanding and absorbing the wastes by using capillary action. However, the waste absorber 22 is not limited thereto, and may use all porous materials capable of absorbing the wastes. Therefore, the wastes once absorbed by the waste absorber 22 may be safely stored inside without leaking to the outside.

For example, the waste absorber 22 may include a coagulant that coagulates to a gel state when mixed with moisture, in order to prevent leakage of the wastes or environmental pollution caused by the wastes. Therefore, the wastes absorbed by the waste absorber 22 may coagulate to prevent leakage and be reduced in moisture to prevent bacterial growth or decay.

In addition, the waste absorber 22 may include at least one of a disinfectant, a sanitizer, a deodorant, a preservative, bleach, an air freshener, a coagulant, and combinations thereof.

Therefore, due to the above-mentioned various chemicals, the wastes absorbed by the waste absorber 22 may not only prevent bacterial growth or decay but also prevent various odors, discoloration, and pollution.

For example, as illustrated in FIG. 5, the waste storage case 21 may include a middle case 21-1 detachably coupled to a bottom surface of the cartridge body 10, and a lower case 21-2 having a top opening to contain the waste absorber 22 and detachably coupled to the middle case 21-1.

Therefore, a user may easily assemble the waste storage case 21 to the cartridge body 10 to use the waste storage case 21, and easily disassemble the waste storage case 21 from the cartridge body 10 to dispose of only the waste storage case 21.

For example, as illustrated in FIGS. 4 and 5, a waste passage P through which the wastes pass may be provided through a side surface of the waste storage case 21, and a check valve 23 may be mounted in the waste passage P to prevent backflow of the wastes.

Therefore, leakage of the wastes may be fundamentally prevented using the check valve 23 including, for example, a diaphragm.

Meanwhile, as illustrated in FIG. 2, the temporary storage 20 may be provided under a part including at least one of the sample container 13, the reagent containers 14, the mixed solution container 15, the diluent container 16, the washing solution containers 17, and combinations thereof.

Therefore, the temporary storage 20 may be separate from the reaction well 1 to fundamentally prevent the wastes from adversely affecting the reaction well 1 when the reactions occur in the reaction well 1.

Accordingly, aesthetic appearance may be achieved by temporarily storing the wastes in the reaction well cartridge device 100 to be disposed of after a single use, and excellent hygienic properties may be achieved by preventing bacterial growth, decay, or leakage of the wastes, thereby increasing the safety of bioassays and preventing environmental pollution.

Meanwhile, as illustrated in FIG. 2, the reaction well cartridge system 1000 according to some embodiments of the present invention may include the above-described reaction well cartridge device 100, and a waste transfer device 110 for transferring the wastes from the reaction well 1 to the temporary storage 20.

Herein, as illustrated in FIG. 2, the waste transfer device 110 may include a first transfer line L1 connected from the reaction well 1 to the temporary storage 20, a first valve V1 mounted on the first transfer line L1, and a first pump P1 mounted on the first transfer line L1.

The first valve V1 may use various valves, e.g., a mechanical valve or an electronic valve such as a solenoid valve, and the first pump P1 may use various non-contact or contact pumps, e.g., a diaphragm pump or a diffusion pump.

Therefore, for example, when the first pump P1 operates or the first valve V1 is open after the reactions occur in the reaction well 1, the wastes may be transferred from the reaction well 1 to the temporary storage 20 along the first transfer line L1, temporarily stored in the temporary storage 20, and then individually disposed of together with the cartridge body 10.

Herein, as an example of the reactions occurring in the reaction well 1, a binding inducer capable of inducing adsorption or biospecific binding may be selected as interleukin-6 (IL-6) specific antibodies and immobilized on the surface in the reaction well 1. For example, immobilization may be induced on the surface for 30 minutes by using 30 uL of a sample solution such as 1% glutaraldehyde diluted with 0.1 M 2-(N-morpholino)ethanesulfonic acid (MES) (pH 6.1).

Then, a washing process may be performed once for 10 minutes by using 30 uL of a washing solution provided as 0.1 M MES (pH 6.1). 30 uL of 10 ug/mL IL-6 specific antibodies may be added to induce a reaction between glutaraldehyde and the IL-6 antibodies for 30 minutes.

Then, a sample solution of 2% bis(trimethylsilyl)acetamide (BSA) and 0.05% TritonX100-0.1 M Tris (pH 7.6) may be added to induce a reaction twice for 10 minutes, and functional groups of glutaraldehyde which do not participate in binding on the surface in the reaction well 1 may be removed.

Then, 30 uL of IL-6 antigens may be added at every desired concentration to induce binding with the antibodies for 30 minutes. 30 uL of a washing solution provided as 0.05% TritonX100-Tris (pH 7.6) may be added to perform a washing process once for 10 minutes.

Then, 30 uL of 2 ug/mL antibody-biotin polymer may be added to induce biospecific binding for 30 minutes. 30 uL of a washing solution provided as 0.05% TritonX100-Tris (pH 7.6) may be added again to perform a washing process once for 10 minutes.

Then, 30 uL of streptavidin-horseradish peroxidase (HRP) polymer may be added to induce biospecific binding between the antibody-biotin polymer and the streptavidin-HRP polymer for 30 minutes.

Then, 30 uL of a washing solution provided as 0.05% TritonX100-Tris (pH 7.6) may be added to perform a washing process three times at intervals of 10 minutes, such that streptavidin-HRP which does not participate in binding may be washed away.

Lastly, 30 uL of a substrate which reacts with the enzyme may be added to induce a reaction for 15 minutes, and the amount of the IL-6 antigens may be quantified. In this case, an assay method such as absorption, fluorescence, or chemiluminescence may be determined based on the type of the substrate which reacts with the enzyme.

Therefore, because a washing process is performed more than once in the reaction well 1 of the present invention to repeatedly reduce a background signal caused during immunoassay, signal sensitivity may be increased, an assay device may be simplified, applicability to microchip-based assay devices required to wash residues (e.g., antigens, antibodies, or probes) unavoidably produced after biological reaction, e.g., sandwich immunoassay and nucleotide detection devices, may be achieved, the washing process may be rapidly and simply performed using an active pump, and biochemical analysis may be enabled without an additional suction process for removing a washing solution during the washing process.

The wastes produced in the above process may be temporarily stored in the temporary storage 20 and then individually disposed of together with the cartridge body 10.

Figure 6:
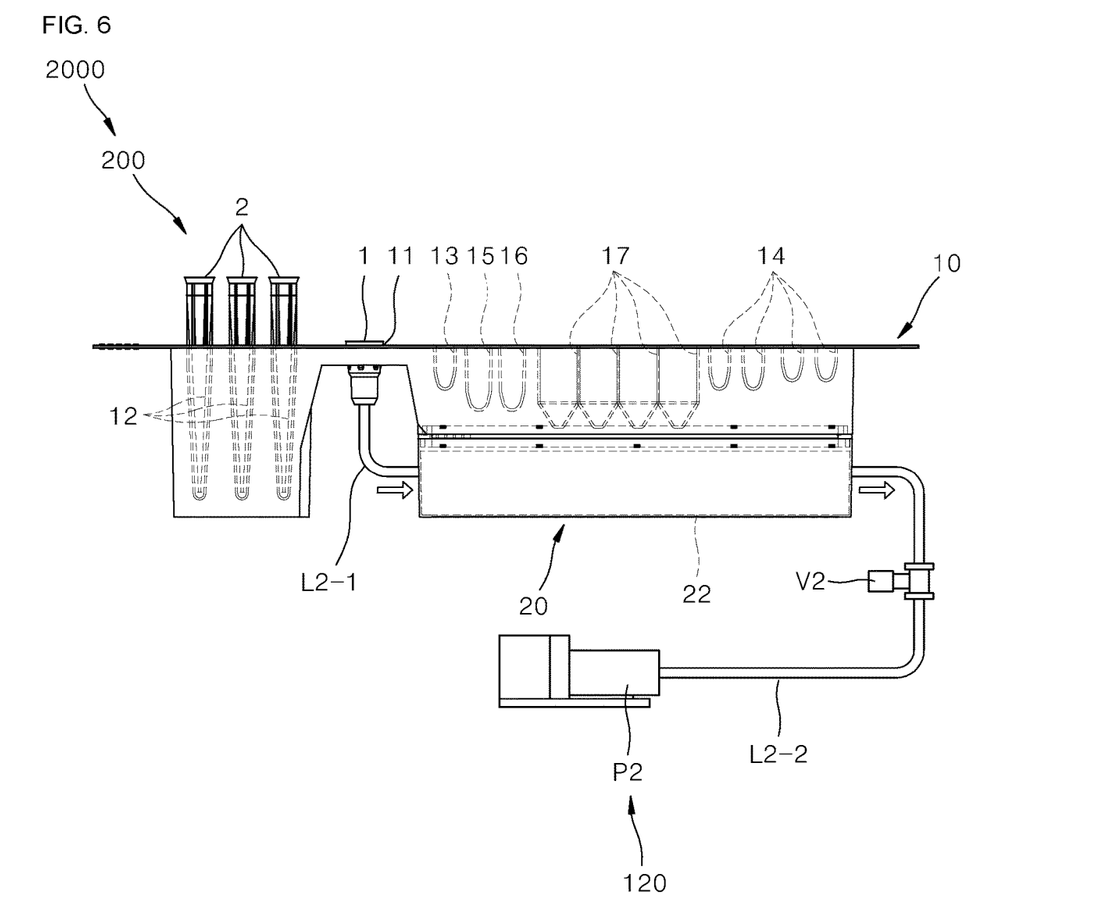
FIG. 6 is a front view of a reaction well cartridge device and a reaction well cartridge system according to other embodiments of the present invention.

FIG. 6 is a front view of a reaction well cartridge device 200 and a reaction well cartridge system 2000 according to other embodiments of the present invention.

As illustrated in FIG. 6, the temporary storage 20 of the reaction well cartridge device 200 and the reaction well cartridge system 2000 according to other embodiments of the present invention may be provided under a part including at least one of the sample container 13, the reagent containers 14, the mixed solution container 15, the diluent container 16, the washing solution containers 17, and combinations thereof, and a waste transfer device 120 may include a second-1 transfer line L2-1 curvedly connected from the reaction well 1 to the temporary storage 20, a second-2 transfer line L2-2 connected from the temporary storage 20 to an external air vent, a second valve V2 mounted on the second-2 transfer line L2-2, and a second pump P2 mounted on the second-2 transfer line L2-2.

The second valve V2 may use various valves, e.g., a mechanical valve or an electronic valve such as a solenoid valve, and the second pump P2 may use various non-contact or contact pumps, e.g., a diaphragm pump or a diffusion pump.

Therefore, for example, when the second pump P2 operates or the second valve V2 is open after reactions occur in the reaction well 1, wastes may be transferred from the reaction well 1 to the temporary storage 20 along the second-1 transfer line L2-1 and stored in the temporary storage 20, and only air may be discharged to the outside through the second-2 transfer line L2-2. Therefore, the wastes may be temporarily stored in the temporary storage 20 and then individually disposed of together with the cartridge body 10.

Figure 7:
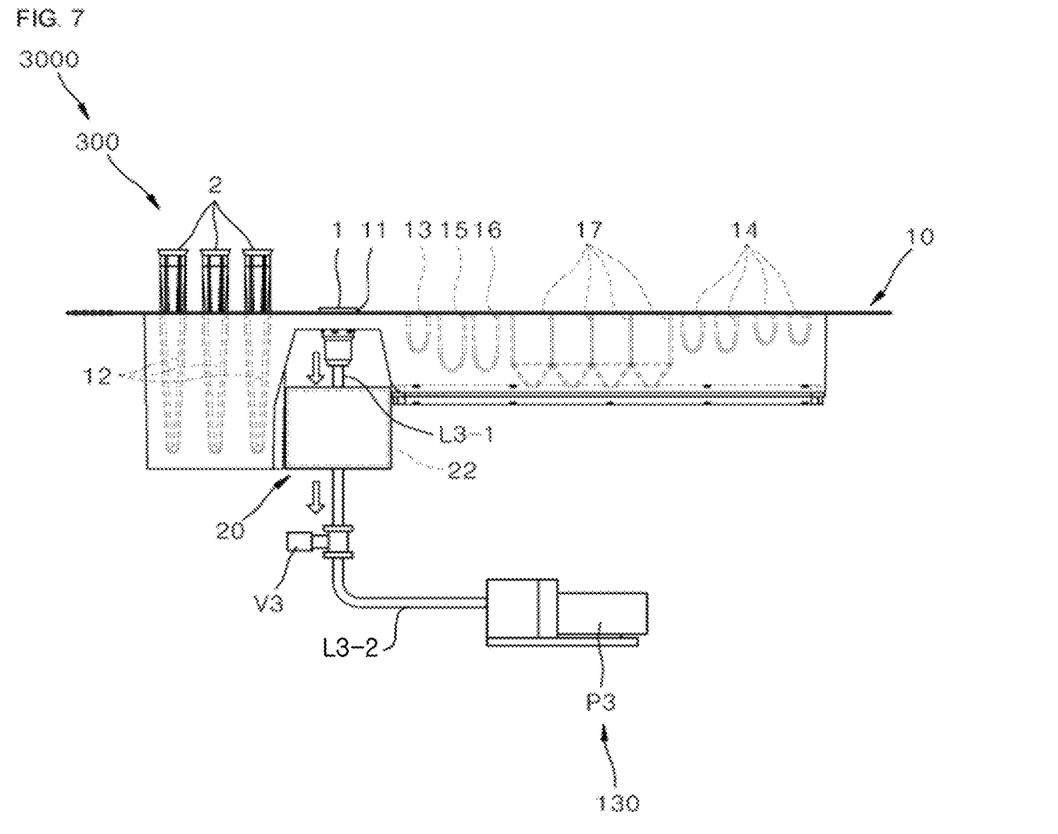
FIG. 7 is a front view of a reaction well cartridge device and a reaction well cartridge system according to still other embodiments of the present invention.

FIG. 7 is a front view of a reaction well cartridge device 300 and a reaction well cartridge system 3000 according to still other embodiments of the present invention.

As illustrated in FIG. 7, the temporary storage 20 of the reaction well cartridge device 300 and the reaction well cartridge system 3000 according to still other embodiments of the present invention may be provided under the reaction well container 11 so as to be indirectly or directly connected to the reaction well 1, and a waste transfer device 130 may include a third-1 transfer line L3-1 linearly connected from the reaction well 1 to the temporary storage 20, a third-2 transfer line L3-2 connected from the temporary storage 20 to an external air vent, a third valve V3 mounted on the third-2 transfer line L3-2, and a third pump P3 mounted on the third-2 transfer line L3-2.

The third valve V3 may use various valves, e.g., a mechanical valve or an electronic valve such as a solenoid valve, and the third pump P3 may use various non-contact or contact pumps, e.g., a diaphragm pump or a diffusion pump.

Therefore, for example, when the third pump P3 operates or the third valve V3 is open after reactions occur in the reaction well 1, wastes may be transferred from the reaction well 1 to the temporary storage 20 along the third-1 transfer line L3-1 and stored in the temporary storage 20, and only air may be discharged to the outside through the third-2 transfer line L3-2. Therefore, the wastes may be temporarily stored in the temporary storage 20 and then individually disposed of together with the cartridge body 10.

Accordingly, fluid control for biochemical reaction in the reaction well 1 may be simplified, manufacturing of devices may be facilitated, the flow, stop, and washing of a fluid may be controlled using an active pump, and the number of washing processes may be freely adjusted.

While the present invention has been particularly shown and described with reference to embodiments thereof, it will be understood by one of ordinary skill in the art that various changes in form and details may be made therein without departing from the scope of the present invention as defined by the following claims.

INDUSTRIAL APPLICABILITY

As described above, according to some embodiments of the present invention, fluid control for biochemical reaction in a reaction well may be simplified, manufacturing of devices may be facilitated, the flow, stop, and washing of a fluid may be controlled using an active pump, the number of washing processes may be freely adjusted, aesthetic appearance may be achieved by temporarily storing wastes in a cartridge to be disposed of after a single use, and hygienic properties may be achieved by preventing bacterial growth, decay, or leakage of the wastes, thereby increasing the safety of bioassays and preventing environmental pollution.

The invention claimed is:

1. A reaction well cartridge device comprising:
at least one of a reaction well where biological reactions occur, pipette tips, a sample, reagents, a mixed solution of the sample and the reagents, a diluent, and washing solutions;
a cartridge body comprising at least one container, each of the at least one container open in one direction and configured to accommodate contents, wherein the at least one container includes at least one of a reaction well container containing the reaction well, a pipette tip container containing the pipette tips, a sample container containing the sample, a reagent container containing the reagents, a mixed solution container containing the mixed solution of the sample and the reagents, a diluent container containing the diluent, and a washing solution container containing the washing solutions; and
a temporary storage container detachably coupled to the cartridge body configured to temporarily store wastes produced after the biological reactions occur in the reaction well,
wherein the temporary storage container comprises:
a waste storage case; and
a waste absorber disposed inside the waste storage case configured to absorb and prevent leakage of the wastes.

2. The reaction well cartridge device of claim 1, wherein the waste absorber comprises a dry compressed sponge configured to expand and absorb the wastes.

3. The reaction well cartridge device of claim 1, wherein the waste absorber further comprises a coagulant configured to coagulate when mixed with moisture, and prevent leakage of the wastes and environmental pollution caused by the wastes.

4. The reaction well cartridge device of claim 1, wherein the waste absorber further comprises at least one of a disinfectant, a sanitizer, a deodorant, a preservative, a bleach, an air freshener, and a coagulant.

5. The reaction well cartridge device of claim 1, wherein the waste storage case further comprises:
a middle case detachably interposed between the cartridge body and a lower case; and
the lower case detachably coupled to the middle case, wherein the lower case defines an internal space configured to contain the waste absorber.

6. The reaction well cartridge device of claim 1, wherein the waste storage case further comprises:
a waste passage defined on a side surface of the waste storage case configured to allow the wastes to pass through; and
a check valve disposed on the waste passage configured to prevent backflow of the wastes flowing through the waste passage.

7. The reaction well cartridge device of claim 1, wherein the temporary storage container is detachably coupled to at least one of the sample container, the reagent container, the mixed solution container, the diluent container, and the washing solution container.

8. The reaction well cartridge device of claim 1, wherein the temporary storage container is detachably coupled to the reaction well container and is configured to connect directly or indirectly to the reaction well.

9. A reaction well cartridge system comprising:
  at least one of a reaction well where biological reactions occur, pipette tips, a sample. reagents, a mixed solution of the sample and the reagents a diluent, and washing solutions;
  a cartridge body comprising at least one container, each of the at least one container open in one direction and configured to accommodate contents, wherein the at least one container includes at least one of a reaction well container containing the reaction well, a pipette tip container containing the pipette tips, a sample container containing the sample, a reagent container containing the reagents, a mixed solution container containing the mixed solution of the sample and the reagents, a diluent container containing the diluent, and a washing solution container containing the washing solutions;
  a temporary storage container detachably coupled to the cartridge body configured to temporarily store wastes produced after the reactions occur in the reaction well; and
  a waste transfer device configured to deliver the wastes from the reaction well to the temporary storage container,
  wherein the temporary storage container comprises:
    a waste storage case; and
    a waste absorber disposed inside the waste storage case configured to absorb and prevent leakage of the wastes.

10. The reaction well cartridge system of claim 9, wherein the waste transfer device comprises:
  a first transfer line connecting the reaction well to the temporary storage container;
  a first valve disposed on the first transfer line; and
  a first pump disposed on the first transfer line.

11. The reaction well cartridge system of claim 9, wherein the temporary storage container is detachably coupled to at least one of the sample container, the reagent container, the mixed solution container, the diluent container, and the washing solution container, and
  wherein the waste transfer device further comprises:
    a first part of a second transfer line curvedly connecting the reaction well to the temporary storage container;
    a second part of the second transfer line connected from the temporary storage container to an external air vent;
    a second valve disposed on the second part of the second transfer line; and
    a second pump disposed on the second part of the second transfer line.

12. The reaction well cartridge system of claim 9, wherein the temporary storage container is detachably coupled to the reaction well container and is configured to connect directly or indirectly to the reaction well, and
  wherein the waste transfer device further comprises:
    a first part of a third transfer line linearly connecting the reaction well to the temporary storage container;
    a second part of the third transfer line connected from the temporary storage container to an external air vent;
    a third valve disposed on the second part of the third transfer line; and
    a third pump disposed on the second part of the third transfer line.

13. A reaction well cartridge system comprising:
  at least one of a reaction well where biological reactions occur, pipette tips, a sample, reagents, a mixed solution of the sample and the reagents, a diluent, and washing solutions;
  a cartridge body comprising at least one container, each of the at least one container open in one direction and configured to accommodate contents, wherein the at least one container includes at least one of a reaction well container containing the reaction well, a pipette tip container containing the pipette tips, a sample container containing the sample, a reagent container containing the reagents, a mixed solution container containing the mixed solution of the sample and the reagents, a diluent container containing the diluent, and a washing solution container containing the washing solutions;
  a temporary storage container detachably coupled to the cartridge body configured to temporarily store wastes produced after the biological reactions occur in the reaction well; and
  a waste transfer device configured to deliver the wastes from the reaction well to the temporary storage container,
  wherein the temporary storage container comprises:
    a waste storage case comprising a middle case detachably interposed between the cartridge body and a lower case, and the lower case detachably coupled to the middle case,
    wherein the lower case defines an internal space configured to contain a waste absorber;
    the waste absorber disposed inside the internal space of the waste storage case configured to absorb and prevent leakage of the wastes;
    a waste passage defined on a side surface of the waste storage case configured to allow the wastes to pass through; and
    a check valve disposed on the waste passage configured to prevent backflow of the wastes flowing through the waste passage, and
  wherein the waste transfer device comprises a first transfer line connecting the reaction well to the temporary storage container.

14. The reaction well cartridge system of claim 13, wherein the waste transfer device further comprises:
  a first valve disposed on the first transfer line; and
  a first pump disposed on the first transfer line.

15. The reaction well cartridge system of claim 13, wherein the waste absorber comprises a dry compressed sponge configured to expand and absorb the wastes.

16. The reaction well cartridge system of claim 13, wherein the waste absorber comprises a porous material capable of absorbing the wastes.

17. The reaction well cartridge system of claim 13, wherein the waste absorber further comprises a coagulant configured to coagulate when mixed with moisture, and prevent leakage of the wastes and environmental pollution caused by the wastes.

18. The reaction well cartridge system of claim 13, wherein the waste absorber further comprises at least one of a disinfectant, a sanitizer, a deodorant, a preservative, a bleach, an air freshener, and a coagulant.

19. The reaction well cartridge system of claim 13, wherein the temporary storage container is detachably coupled to at least one of the sample container, the reagent container, the mixed solution container, the diluent container, and the washing solution container.

20. The reaction well cartridge system of claim 13, wherein the temporary storage container is detachably coupled to the reaction well container and is configured to connect directly or indirectly to the reaction well.

* * * * *